United States Patent
Dhanani et al.

(10) Patent No.: US 11,276,891 B2
(45) Date of Patent: Mar. 15, 2022

(54) LITHIUM ION BATTERY PROTECTION SYSTEM

(71) Applicant: Kidde Technologies, Inc., Wilson, NC (US)

(72) Inventors: Sandip Dhanani, Knightdale, NC (US); Stefan Coreth, Roanoke Rapids, NC (US); Terry Simpson, Wake Forest, NC (US); Amanda J. Daly, Cary, NC (US)

(73) Assignee: KIDDE TECHNOLOGIES, INC., Wilson, NC (US)

(*) Notice: Subject to any disclaimer, the term of this patent is extended or adjusted under 35 U.S.C. 154(b) by 218 days.

(21) Appl. No.: 16/545,657

(22) Filed: Aug. 20, 2019

(65) Prior Publication Data
US 2021/0057784 A1 Feb. 25, 2021

(51) Int. Cl.
| H01M 10/48 | (2006.01) |
| H01M 10/0525 | (2010.01) |
| H01M 10/42 | (2006.01) |
| G01N 21/77 | (2006.01) |
| G01N 33/00 | (2006.01) |

(52) U.S. Cl.
CPC ........ *H01M 10/48* (2013.01); *G01N 21/7703* (2013.01); *G01N 33/0027* (2013.01); *H01M 10/0525* (2013.01); *H01M 10/4235* (2013.01)

(58) Field of Classification Search
CPC .......... H01M 10/052; H01M 10/0525; H01M 10/4235; H01M 10/48; H01M 50/572; G01N 21/7703; G01N 21/783; G01N 21/8507; G01N 33/0027
See application file for complete search history.

(56) References Cited

U.S. PATENT DOCUMENTS

| 9,209,494 | B2 | 12/2015 | Kiesel et al. |
| 9,553,465 | B2 | 1/2017 | Raghavan et al. |
| 9,583,796 | B2 | 2/2017 | Saha et al. |
| 9,677,916 | B2 | 6/2017 | Hegyi et al. |
| 10,107,867 | B2 | 10/2018 | Elian et al. |
| 2010/0135355 | A1 | 6/2010 | Hermann et al. |
| 2012/0312562 | A1 | 12/2012 | Woehrle et al. |
| 2014/0203783 | A1 | 7/2014 | Kiesel et al. |

(Continued)

FOREIGN PATENT DOCUMENTS

| EP | 2937928 A1 | 10/2015 |
| EP | 3517938 A1 | 7/2019 |

OTHER PUBLICATIONS

Extended European Search Report issued in Application No. 19212804.9 dated Jun. 30, 2020, 7 pages.

*Primary Examiner* — Carlos Barcena
(74) *Attorney, Agent, or Firm* — Cantor Colburn LLP

(57) ABSTRACT

A system is disclosed for protection of a lithium ion battery. The system includes a first light source and a first optical guide including first and second ends. The first optical guide is in optical communication with the light source at the first end of the first optical guide. A first material is disposed on an exterior surface of the first optical guide in fluid communication with an exterior surface of the lithium ion battery. The first material is optically responsive to a first gas indicative of an overheat condition or combustion of the lithium ion battery. A first light detector is in optical communication with the second end of the first optical guide.

3 Claims, 2 Drawing Sheets

(56) References Cited

U.S. PATENT DOCUMENTS

2015/0303723 A1\* 10/2015 Raghavan ............... H02J 7/007
                                                    320/107
2016/0028129 A1   1/2016 Raghavan et al.
2018/0003685 A1\* 1/2018 Cummings ........ G01N 33/0036

\* cited by examiner

LITHIUM ION BATTERY PROTECTION SYSTEM

BACKGROUND

The following description relates generally to protection systems for lithium ion batteries and, more specifically, to a system for early detection of a fire or an overheated condition in a lithium ion battery.

A lithium ion battery is a rechargeable battery and typically includes a volumetric body in which an electrolyte is provided between positive electrode plates and negative electrode plates. The positive electrode plates can be interleaved between the negative electrode plates in a face-to-face arrangement. When the battery is being discharged, lithium ions move from the negative electrode to the positive electrode. During recharging, the lithium ions move back to the negative electrode.

An ongoing issue with certain lithium ion batteries is their tendency to overheat. When this happens, the result can lead to combustion and resultant fire that can damage the lithium ion battery as well as the surrounding objects (i.e., components of an electric vehicle or an airplane). As such, despite recent progress and improvement in lithium ion battery safety features, fire suppression systems for use with lithium ion batteries are and remain useful. However, even with effective fire suppression, the early detection of lithium ion battery fires is a major key to suppression.

BRIEF DESCRIPTION

A system is disclosed for protection of a lithium ion battery. The system includes a first light source and a first optical guide including first and second ends. The first optical guide is in optical communication with the light source at the first end of the first optical guide. A first material is disposed on an exterior surface of the first optical guide in fluid communication with an exterior surface of the lithium ion battery. The first material is optically responsive to a first gas indicative of an overheat condition or combustion of the lithium ion battery. A first light detector is in optical communication with the second end of the first optical guide.

In some aspects, the first optical guide includes a first fiber optic element including a first core that is optically transmissive and a first cladding optically coupled to the first core configured to reflect light from the first core at an interface between the first core and the first cladding. The first material is optically coupled to the first core in place of the cladding at the first optical guide exterior surface in fluid communication with the exterior surface of the lithium battery.

In any one or combination of the foregoing aspects, the first material is optically responsive to said first gas selected from hydrogen fluoride, carbon dioxide, carbon monoxide, battery electrolytes such as ethylene carbonate, dimethylcarbonate, ethylmethylcarbonate, and diethylcarbonate.

In any one or combination of the foregoing aspects, the first core comprises a polymer, and the first material comprises silica that is optically responsive to hydrogen fluoride.

In any one or combination of the foregoing aspects, the first core comprises silica, and the first material comprises a dye that is optically responsive to carbon dioxide.

In any one or combination of the foregoing aspects, the lithium ion battery comprises a case, and a lithium ion battery cell disposed inside the case.

In any one or combination of the foregoing aspects, the lithium ion battery and the first material on the exterior surface of the first optical guide are disposed within a housing.

In any one or combination of the foregoing aspects, the housing is enclosed.

In any one or combination of the foregoing aspects, the housing includes a gas flow path from the exterior of the housing to the exterior surface of the lithium battery to the first material on the exterior surface of the first optical guide.

In any one or combination of the foregoing aspects, the system further includes a reference optical guide including an exterior surface without the second material, said reference guide exterior surface in fluid communication with the exterior surface of the lithium battery.

In any one or combination of the foregoing aspects, the system further includes a second optical guide including first and second ends. The first end of the second optical guide is in optical communication with the first light source, or the system includes a second light source and the first end of the second optical guide is in optical communication with the second light source. A second material is disposed on an exterior surface of the second optical guide in fluid communication with the exterior surface of the lithium battery. The second material is optically responsive to a second gas indicative of an overheat condition or combustion of the lithium ion battery. A second light detector is in optical communication with the second end of the first optical guide.

In any one or combination of the foregoing aspects, the first end of the second optical guide is in optical communication with the first light source.

In any one or combination of the foregoing aspects including the second light source, wherein the first end of the first optical guide is in optical communication with the first light source, and the first end of the second optical guide is in optical communication with the second light source.

In any one or combination of the foregoing aspects, the first optical guide comprises a first fiber optic element including a first core that is optically transmissive and a first cladding optically coupled to the first core configured to reflect light from the first core at an interface between the first core and the first cladding, wherein the first material is optically coupled to the first core in place of the first cladding at the exterior surface in fluid communication with the first optical guide exterior surface of the lithium battery. The second optical guide comprises a second fiber optic element including a second core that is optically transmissive and a second cladding optically coupled to the second core configured to reflect light from the second core at an interface between the second core and the second cladding, wherein the second material is optically coupled to the second core in place of the second cladding at the second optical guide exterior surface in fluid communication with the exterior surface of the lithium battery.

In any one or combination of the foregoing aspects, the first material is optically responsive to the first gas selected from hydrogen fluoride, carbon dioxide carbon monoxide, battery electrolytes such as ethylene carbonate, dimethylcarbonate, ethylmethylcarbonate, and diethylcarbonate, and the second material is optically responsive to the second gas different than the first gas and selected from hydrogen fluoride, carbon dioxide carbon monoxide, ethylene carbonate, dimethylcarbonate, ethylmethylcarbonate, and diethylcarbonate.

In any one or combination of the foregoing aspects, the first core comprises a polymer and the first material comprises silica that is optically responsive to hydrogen fluoride, and the second core comprises silica, and the second material comprises a dye that is optically responsive to carbon dioxide.

Also disclosed is a method of making a system for protection of a lithium ion battery. According to the method, a first optical guide including first and second ends and a first material optically responsive to a first gas indicative of an overheat condition or combustion of the lithium ion battery on an exterior surface of the first optical guide, is disposed with the first material in fluid communication with an exterior surface of the lithium battery. A light source is disposed in optical communication with the first end of the first optical guide. A first light detector is disposed in optical communication with the second end of the first optical guide.

In some aspects, the method includes disposing the lithium ion battery and the first material on the exterior surface of the first optical guide within a housing.

In any one or combination of the foregoing aspects, the method further includes disposing a second optical guide including first and second ends and a second material optically responsive to a second gas indicative of an overheat condition or combustion of the lithium ion battery on an exterior surface of the second optical guide, with the second material in fluid communication with an exterior surface of the lithium battery. The first light source or a second light source is disposed in optical communication with the first end of the second optical guide, or a second light detector is disposed in optical communication with the second end of the second optical guide. A second light detector is disposed in optical communication with the second end of the first optical guide.

In any one or combination of the foregoing aspects, the first optical guide, the first light source, and the first light detector (and optional the second optical guide, the second light source, and the second light detector) are installed as a retrofit to an operational lithium battery connected to a power sink and a recharging power source.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more aspects of the disclosed apparatus and method are presented herein by way of exemplification and not limitation with reference to the Figures.

Figure 1:
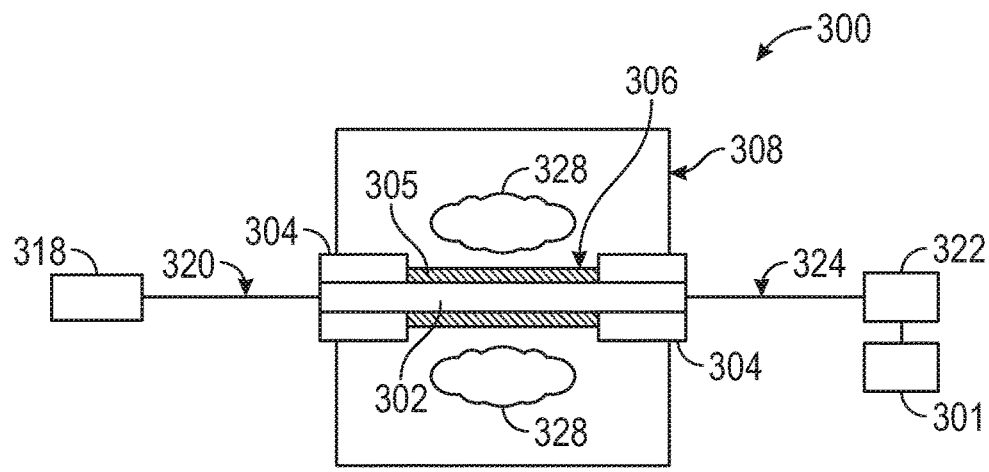
FIG. 1 is a schematic illustration of an example of optical guide.

With reference now to FIG. 1, an example embodiment of a sensor assembly 300 is schematically shown. As shown in FIG. 1, an optical guide in the form of a fiber optic element shown in a cross-sectional view with a fiber optic element core 302 and a fiber optic element cladding 304 around the core 302. The core can be made of various types of glass (e.g., silica) or polymers (e.g., polymethyl methacrylate, polystyrene) with high transmissivity and appropriate refractive indices to guide light within the core axially along the length of the fiber. This is accomplished with a refractive index differential at the interface along which the core is optically coupled to the cladding such that light transmitting through the core that is incident on the interface totally reflected back into the core according to Snell's Law. This phenomenon is known as total internal reflection, and is the basis for fiber optic technology, camera and binocular prisms, automotive windshield rain sensors, and numerous other technologies. Examples of materials for cladding of glass cores include but are not limited to urethane acrylates or polyimides, and examples of materials for polymer cores include but are not limited to silicone resins.

With continued reference to FIG. 1, a portion of the fiber optic element has the cladding 304 replaced with a material 306 on an optical guide exterior surface 305. The material 306 is optically responsive to a gas indicative of an overheat condition or combustion of a lithium ion battery. Examples of such gases include but are not limited to hydrogen fluoride, carbon dioxide, carbon monoxide, battery electrolytes such as ethylene carbonate, dimethylcarbonate, ethylmethylcarbonate, and diethylcarbonate. Examples of materials for the material 306 include but are not limited to silica (optically responsive to hydrogen fluoride by etching of the silica by hydrogen fluoride, and which can be disposed on a polymer core by techniques such as low-pressure plasma-enhanced chemical vapor deposition) or fluorescent or absorptive dyes in a matrix such as a polymer matrix or sol-gel (e.g., silica gel) matrix, which can be disposed on a silica core. Such dyes can be optically responsive to components such as carbon dioxide and organic carbonates through a change in pH. Other compounds with functional groups that interact with the gas being tested for can also be utilized in the matrix of the cladding replacement material to provide an optical response indicative of the presence of the species of interest. Examples of fluorescent dyes include but are not limited to fluorescein or HPTS (8-hydroxypyrene-1,3,6-trisulfonic acid). Examples of absorptive dyes include but are not limited to methyl red, phenol red, thymol blue, or bromothymol blue. Examples of matrices include but are not limited to polystyrene, polymethyl methacrylate, or silicone resins. Exposure of the dye(s) to a gas indicative of overheat or combustion such as carbon dioxide will change the absorption spectrum or fluorescent emission of the dye(s), causing a change to the characteristics of light transmitted through the core 302.

The portion of the optical guide with the material 306 can be disposed in a detection space 308 that is in fluid communication with an exterior surface of a lithium battery. The detection space 308 can be inside of a housing as will described below or can simply be a non-enclosed air space that is sufficiently proximate to an exterior surface of a lithium ion battery to be in fluidic communication therewith. The core 302 is optically connected on one end to a light source 318 (e.g., a laser at a wavelength, e.g., a green, red or near-infrared (NIR) laser (e.g., 520 nm, 620 nm, 650 nm), that is affected by the optical response of the material 306 to a gas 328 indicative of an overheat condition or combustion of the lithium ion battery. The light source 318 is connected to the core 302 through an optical connection 320. The optional connection 320 can be any type of optical connection such as a fiber optic cable extension of the fiber optic element in the detection space 308, or a direct connection of the light source 318 to the fiber optic element in the detection space 308. The core 302 is optically connected on another end to a light detector 322 through an optical connection 324, which can be the same or different type of optical connection as the optical connection 320. An electronic processing unit 301 is shown connected to read the output of the light detector 322, and can be operationally connected (e.g., through wired connections (not shown) or through wireless connections) to other system components such a sampling pump or fan (not shown) that can direct air flow past from the lithium ion battery external surface to the detection space 308, or to other on-board systems and operational structures.

Figure 2:
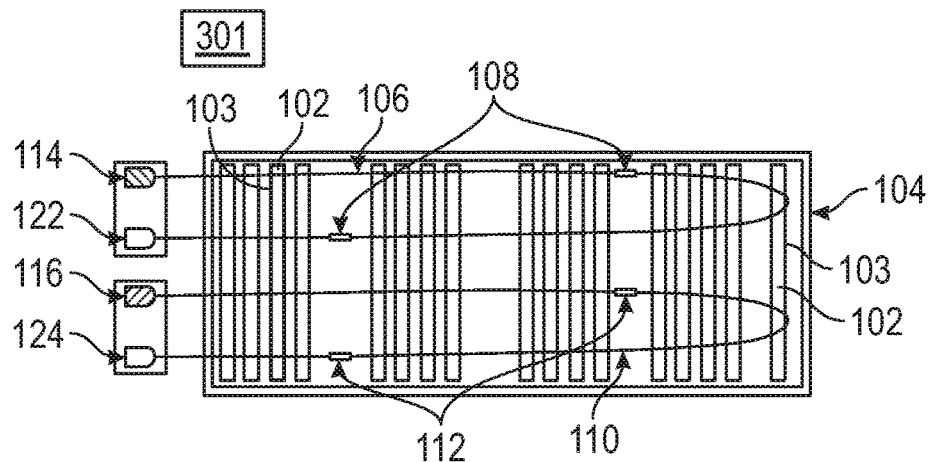
FIG. 2 is a schematic illustration of an example of a system for protection of a lithium ion battery.
Figure 3:
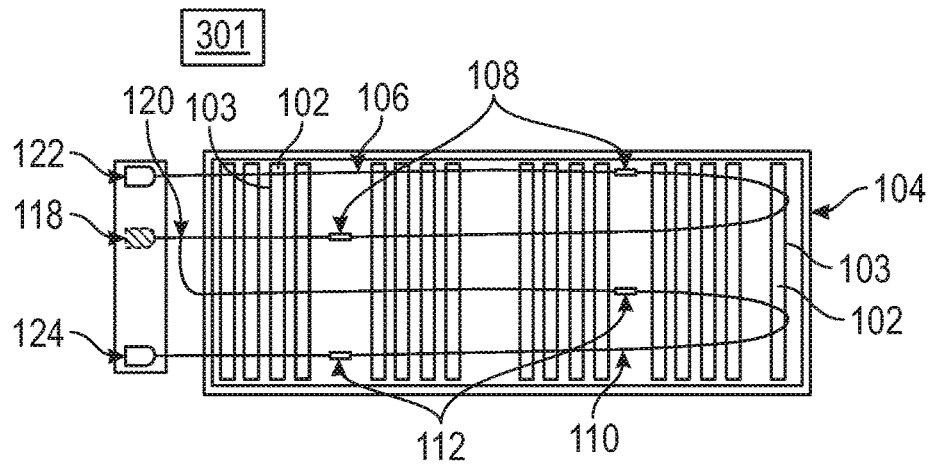
FIG. 3 is a schematic illustration of another example of a system for protection of a lithium ion battery.

In some embodiments, the protection system can include multiple optical guides as sensors for different gases. For example, in some aspects, the protection system can include multiple optical guides configured for detection of multiple gases selected from hydrogen fluoride, carbon dioxide, carbon monoxide, battery electrolytes such as ethylene carbonate, dimethylcarbonate, ethylmethylcarbonate, or diethylcarbonate. In some aspects, the protection system can include two optical guides configured for detection of two gases selected from hydrogen fluoride, carbon dioxide, carbon monoxide, battery electrolytes such as ethylene carbonate, dimethylcarbonate, ethylmethylcarbonate, or diethylcarbonate. In some aspects, the protection system can include an optical guide for detection of carbon dioxide and an optical guide for detection of hydrogen fluoride. FIGS. 2 and 3 schematically show example embodiments of protection systems with two optical guides for detecting different gases indicative of different gases such as hydrogen fluoride and carbon dioxide. As shown in FIGS. 2 and 3, a plurality of lithium ion batteries 102 are disposed in a housing 104 such as a battery pack housing. A first optical guide 106 such as an optical fiber with a silica core and a polymer cladding is disposed in the housing 104 and is routed past the lithium ion batteries 102, which can include one or more lithium ion battery electrochemical cells disposed in a case 103. The lithium ion battery electrochemical inside the case 103 can include an anode comprising a containing first electrolyte including mobile ionizable lithium (e.g., lithium/nickel/manganese/cobalt oxide, lithium nickel/cobalt/aluminum oxide, lithium/manganese oxide), a cathode inside the case 103 comprising a second electrolyte including ionizable lithium ions (e.g., graphite, hard carbon, lithium titanate), and a separator between the anode and the cathode inside the case 103 permeable to lithium ions. At one or more locations 108 along the optical guide 106, the polymer cladding is removed (e.g., by a chemical technique such as solvent removal) and replaced by a material such as a silica that is optically-responsive to a gas such as hydrogen fluoride. A second optical guide 110 such as an optical fiber with a silica core and a polymer cladding is also disposed in the housing 104, routed past the lithium batteries 102. At one or more locations 112 along the optical guide 110, the polymer cladding is removed (e.g., by a chemical technique such as solvent removal) and replaced by a material such as a dye in a polymer matrix that is optically-responsive to a gas such as carbon dioxide. The locations 108 and 112 can be chosen to be in proximity to the exterior surface (i.e., battery case surface) of the lithium ion batteries 102 so as to be in fluidic communication therewith so the optically-responsive material(s) will be contacted by any gas(es) escaping from the battery case(s).

As further shown in FIGS. 2 and 3, the optical guides 106 and 110 are optically connected to a light source such as an LED and to a light detector such as a photodiode. As shown in FIG. 2, each of the optical guides 106 and 110 can be optically coupled to a dedicated light source, with optical guide 106 optically coupled to a light source 114 and optical guide 110 optically coupled to a light source 116. This can allow for each of the optical guides to utilize a wavelength that is optimized for the characteristics of the optical guide and the optically-responsive material (e.g., a red LED such as 650 nm for the optical guide 110 having silica as the optically-responsive material at locations 112, and a green LED such as 520 nm for the optical guide 106 having an absorptive dye as the optically-responsive material at locations 108). As shown in FIG. 3, the optical guides can share a single light source 118 (e.g., a 520 nm or 620 nm LED), connected through a 1×2 optical coupler 120. As shown in FIGS. 2 and 3, each of the optical guides 106 and 110 can be optically coupled to a dedicated light detector, with optical guide 106 optically coupled to a light detector 122 and optical guide 110 optically coupled to a light detector 122, which allows the electronic processing unit 301 to detect the individual responses from each of the optical guides 106 and 110. In some embodiments, one or more reference optical guides (not shown), which can reduce or eliminate the need for pre-calibration. The reference optical guides can be optical guides identical to the optical guides 106 and 110, but without removal and replacement of the cladding.

Figure 4:
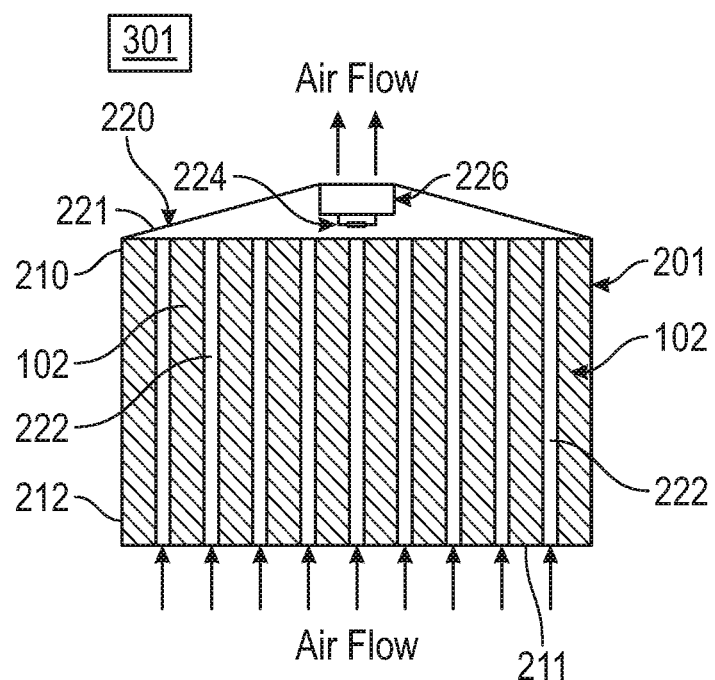
FIG. 4 is a schematic illustration of yet another example of a system for protection of a lithium ion battery.

With reference now to FIG. 4, a protection system shown in which a plurality of lithium ion batteries 102 are disposed in a lithium ion battery rack 201, for example. As shown in FIG. 2, the lithium ion battery rack 201 includes one or more lithium ion battery cells 205 and a volumetric body 210. The volumetric body 210 has a bottom portion 211, sidewalls 212 and a shroud assembly 220 that is supported above the bottom portion 211 by the sidewalls 212.

An optical guide 224 with a portion of cladding removed and replaced with an optically-responsive material that is responsive to a gas indicative of a fire or overheat condition is shown disposed within the space enclosed by the shroud assembly 220. An optical sensor monitoring processor circuit board housing and assembly 226 can be local to the lithium ion battery rack 201 as shown in FIG. 4 or can be remote. In cases where the interrogator board housing and assembly 226 and/or the controller 301 is local, it can in some aspects be powered by the lithium ion batteries 102. In any case, the shroud assembly 220 is attached to the sidewalls 212 of the volumetric body 210 and is configured to direct gases that can be produced and given off by the one or more lithium ion batteries 102 prior to and during a fire and/or an overheated condition.

The shroud assembly 220 can include a shallow tapered ceiling 221. Where the lithium ion battery rack 201 is generally in its normally upright orientation, the shallow tapered, the ceiling 221 tends to direct the gases can be produced by any of the one or more lithium ion batteries 102 prior to and during a fire and/or overheated condition to rise and flow through air flow channels 222 toward the fire and/or overheated condition detector 101. In some aspects such as where the battery rack 201 is disposed in an environment where the shroud assembly 220 will be disposed at the top, gas flow through the air flow channels can take place by natural convection. In some aspects such as where the battery rack can be subject to varying orientations such as an inverted orientation, a blower (not shown) can be disposed such as at an outlet through the ceiling 21.

Figure 5:
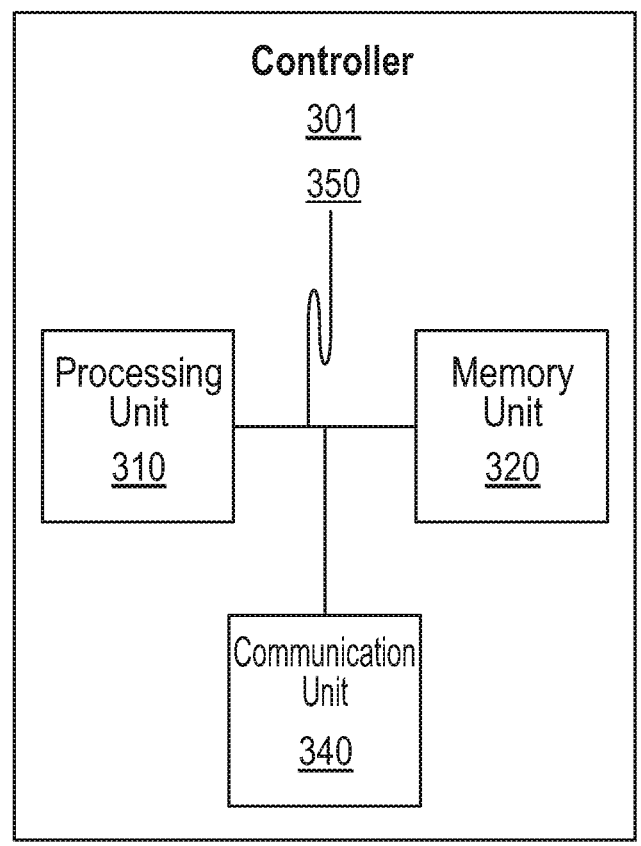
FIG. 5 is a schematic illustration of an example of a controller for a system for protection of a lithium ion battery.

With continued reference to FIGS. 1-4, and with additional reference to FIG. 5, a controller 301 can be provided as a component of the protection system or as part of a larger system such as a motor vehicle control and operating system. In any case, the controller 301 can operably coupled to and disposed in signal communication with each of the light sources and light detectors. The controller 301 can be provided with logic that can execute a multi-criteria algorithm and, as such, the controller 301 can be configured to execute early fire and/or overheated condition detection while ignoring nuisance signals based on readings of various combinations of light detector readings. Signal processing can be performed to discriminate nuisance alarm sources or gases present in normal operations and real lithium ion battery failure events. For example, detection of a single gas such as hydrogen fluoride or carbon dioxide can be the result of battery operation conditions other than an overheat condition or fire condition (such as in the case of detection of hydrogen fluoride or carbon dioxide) or can be the result of exposure to external gas sources (such as in the case of detection of carbon dioxide). However, detection of multiple gases (such as detection of both hydrogen fluoride and carbon dioxide) can be indicative of an overheat condition or combustion.

As shown in FIG. 5, the controller 301 can includes a processing unit 310, a memory unit 320, a communication unit 340 and an input/output (I/O) bus 350. A servo control unit can be provided to allow the processing unit 310 to control certain operations of certain components (e.g., light sources 114, 116, 118). The communication unit 340 allows the processing unit 310 to communicate via wired connections (such as in the case of the controller 301 being local to the lithium ion battery rack 201) or via wireless connections (such as in the case of the controller 301 being remote from the battery rack 201) with components (e.g., the photodetectors 122, 124). The I/O bus 350 can provide for communications and interconnectivity between the processing unit 310, the memory unit 320 and the communications unit 340. The memory unit 320 can have executable instructions stored thereon, which are readable and executable by the processing unit 310. When they are read and executed by the processing unit 310, the executable instructions can cause the processing unit 310 to operate as described herein.

Technical effects and benefits of the enclosure design of the present disclosure are the provision of a detector specifically useful for early detection of lithium ion battery fires. While, typical remotely mounted thermal or smoke detectors will tend to react too slowly to a lithium ion battery fire and/or overheated condition and thus allow the fire to grow to an uncontrollable size, the detector described herein can respond quickly to allow for fire suppression or other mitigation without a substantial risk of false alarms.

As used herein, the term "about" is intended to include the degree of error associated with measurement of the particular quantity based upon the equipment available at the time of filing the application.

The terminology used herein is for the purpose of describing particular aspects only and is not intended to be limiting of the present disclosure. As used herein, the singular forms "a", "an", "the", or "any" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or aspects, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all aspects falling within the scope of the claims.

What is claimed is:

1. A method of making a system for protection of a lithium ion battery, comprising:
    disposing a first optical guide including first and second ends and a first material optically responsive to a first gas indicative of an overheat condition or combustion of the lithium ion battery on an exterior surface of the first optical guide, with the first material in fluid communication with an exterior surface of the lithium battery;
    disposing a first light source in optical communication with the first end of the first optical guide; and
    disposing a first light detector in optical communication with the second end of the first optical guide;
    wherein the first optical guide, the light source, and the first light detector are installed as a retrofit to an operational lithium battery connected to a power sink and a recharging power source.

2. The method of claim 1, wherein the lithium ion battery and the first material on the exterior surface of the first optical guide are disposed within a housing.

3. The method of claim 1, further comprising:
    disposing a second optical guide including first and second ends and a second material optically responsive to a second gas indicative of an overheat condition or combustion of the lithium ion battery on an exterior surface of the second optical guide, with the second material in fluid communication with an exterior surface of the lithium battery;
    disposing the first light source or a second light source in optical communication with the first end of the second optical guide; and
    disposing a second light detector in optical communication with the second end of the second optical guide.

* * * * *